United States Patent [19]

Glenn

[11] Patent Number: Plant 7,551

[45] Date of Patent: Jun. 11, 1991

[54] CHINESE ELM TREE NAMED 'EMER I'

[75] Inventor: Michael M. Glenn, Athens, Ga.

[73] Assignee: Tree Introductions, Inc., Monroe, Ga.

[21] Appl. No.: 335,671

[22] Filed: Apr. 10, 1989

[51] Int. Cl.[5] ..... A01H 5/00

[52] U.S. Cl. ..... Plt./51

[58] Field of Search ..... Plt./51

[56] References Cited

U.S. PATENT DOCUMENTS

P.P. 5,554 9/1984 King ..... Plt. 51

OTHER PUBLICATIONS

Hillier, H. G., *Hilliers Manual of Trees and Shrubs*, pub. A. S. Barnes and Company, N.Y., 1979, p. 401.

Wyman, D., *Trees for American Gardens*, Macmillan Pub. Co., Inc., N.Y., 1974, pp.469 and 470.

Rehder, A., *Manual of Cultivated Trees and Shrubs*, The Macmillan Co., 1960, pp. 181, 182.

*Primary Examiner*—James R. Feyrer

*Attorney, Agent, or Firm*—Klarquist, Sparkman, Campbell, Leigh & Whinston

[57] ABSTRACT

A new and distinct *Ulmus parvifolia* tree which is particularly distinguished in having an attractive, wide-spreading globe shape, being wider than it is tall, having lustrous and leathery dark green leaves, attractive puzzle-like, patchy and colorful quilt-like exfoliating bark patterns. The tree has a very dense and heavy canopy, and scaffold branch crotch angles of 60 to 70 degrees forming a strong tree which endures extremes of weather much better than most other members of the same and other shade tree species.

2 Drawing Sheets

BACKGROUND OF THE INVENTION

The present invention relates to a new and distinct variety of Chinese or lacebark elm, *Ulmus parvifolia*, which is distinguished from all other named forms by the wide-spreading, globe shaped habit, the lustrous leathery dark green leaves, the density of foliage at the ends of the fine branches, and the patchwork, quilt-like bark which exfoliates on one to two inch diameter branches to the upper portion of the mature trunk. The tree was discovered in a cultivated area on the campus of the University of Georgia, Athens, Ga. and nothing is known about its history. The tree is 70 to 75 years old and has not suffered any visible branch or trunk damage.

SUMMARY OF THE VARIETY

'Emer I' is an attractively wide-spreading globe shaped tree which has leaves which are a darker green and more lustrous than those of the species. The tree has endured extremes of weather in the form of hot dry summers, without exhibiting leaf burn, which has caused trees of the same and other shade tree species to display visible damage. The tree forms a very dense, desirable canopy which is comprised of leaves having resistance to Elm Leaf Beetle and Dutch Elm Disease which has ravaged and/or destroyed other elms in the general area. This new variety has been established to be moderately easy to asexually propagate my means of stem cuttings which root with about a 56% take, and to be stable with comparable bud stem and foliage traits of clones being similar to those of the parent tree. The tree is further outstanding in forming wide angle crotches in branch scaffolding to render a tree which will not break apart due to extremes of wind, rain, ice, etc., to form a mature tree of highly attractive and one which will remain so longer than is typical of tree common to the species.

BRIEF DESCRIPTION OF THE DRAWING

Sheet 1 of the drawing depicts the mature parent specimen of the tree in substantially a side view, and shows canopy, tree shape and trunk characteristics; and, Sheet 2 of the drawing shows twigs of 'Emer I' (right side) and of 'Emer II' (left side) and depicts leaf shape and the darker than usual and higher degree of gloss of the leaves of 'Emer I' as compared to 'Emer II' which is more typical of the species.

HORTICULTURAL AND BOTANICAL CHARACTERISTICS (The Royal Horizontal Society Colour Chart was used to described colors where appropriate). The parent tree is characterized by a broad-spread, rounded crown resulting in a pleasing globe-shaped outline, some 30 feet high and 54 feet wide (See FIGS. 1 and 2). The trunk diameter is 3.0 feet and the circumference is 7 feet at a height of 3 feet from the soil line. The bark exfoliates in a puzzle-like pattern exposing light gray, gray-green to orangish-brown colors. The bark is flecked with orangish-brown, corkish lenticels; and the basal two feet of the trunk developed a rough, blockey, gray-black bark.

The leathery, lustrous bark (almost black), green foliage is densely borne at the ends of the fine branches creating a dense canopy. The leaves are more leathery and darker green than the typical phenotype. Fall coloration is a bronze-brown and is not really effective.

VIGOR

The original specimen exhibits no more than 6" of terminal growth per year. Young specimens of rooted, transplanted specimens have grown 24 to 30" in a single growing season.

BRANCHING AND GROWTH HABITS

The variety has high branching density caused by densely borne foliage that occurs on the many fine branches. Typical branch angles is 60 to 70 degrees which is wider than seen in most *Ullmus parvifolia* rendering strong, weather resistant limb structures. Strong, well spaced scaffold branches of such angles account for the tree's attractive broad-spreading globe shape.

DISEASE RESISTANCE

This tree has shown absolutely no symptoms of leaf scorch over the 1986 through 1988 summers which have been some of the hottest and driest on record in the southeast. The tree is also highly resistant to Dutch Elm Disease and Elm Leaf Beetle. It is cold, hardy in Zone 6, USDA.

TAXONOMIC CHARACTERISTICS (A) Leaves: Alternate, simple, 1" to 2" long, ½" to ≃" wide, ovate to slightly obovate, lustrous dark green, almost black-green (yellow-green 147A) above, gray-green (yellow-green 146D) beneath, leathery, acute or obtuse, oblique, simple serrate with rounded serrations, glabrous above and beneath, 10–16 vein pairs; petiole — ⅛" to ¼" long, light green, often pubescent. (See FIG. 2).

(B) Bud: Ovoid, imbricate, chestnut brown, slightly pubescent, ⅛" long, slightly divergent.

(C) Stem: First year: fine textured, terete, brown (gray 201A), pubescent; second year; gray-brown, with small orangish lenticels, glabrous; pith — smith, solid, brown.

(D) Fruit: Samara, oval-rounded, 10 mm long 8 mm wide, with 1 to 2 mm deep notch at distal end, borne in axillary cymose clusters on 2 to 4 mm long pedicels. Fruit's color: light yellow-green (145B) to red-purple (64B). Inconspicuous flowers appear in late August. The fruits or samara ripen in later October.

(E) Trunk: Above 2 feet from the ground, the bark exfoliates in a puzzle-like pattern exposing light-gray (major grayed-green group (197A), gray-green (secondary grays, grade-green group (197B) and (197C) to orangish-brown (grayed-orange (164B) colors, the bark is flecked with rusty-orange (grayed-orange 166C) lenticels. The basel 2 feet of the trunk developed a rough, blocky, gray-black character. It is rounded in cross-section.

(F) Propagation: Cuttings were collected on June 3, 1988 when the terminal leaf was fully mature. Cuttings were stripped of basel foliage, dipped to one inch for 5 seconds in 1.0% KIBA solution, placed in 3 by 3 by 4" cells in 2 perlite: 1 peat mix. Cuttings were then placed under intermittent mist (2½ sec/5 minutes) from 8:00 a.m. to 6:00 p.m. until evaluation on July 21, 1988. "Emerald Isle" rooted 56%. The roots penetrated through drainage holes at the bottom of the rooting container. Root systems of clones are fibrous and dense.

I claim:

1. A new and distinct variety of Elm as herein described and illustrated, primarily characterized by growth habit, leathery lustrous dark-green foliage, denisty of canopy, exfoliating bark, ease of vegetative propagation and resistance to leaf scorch, Dutch Elm Disease and Elm Leaf Beetle.

* * * * *

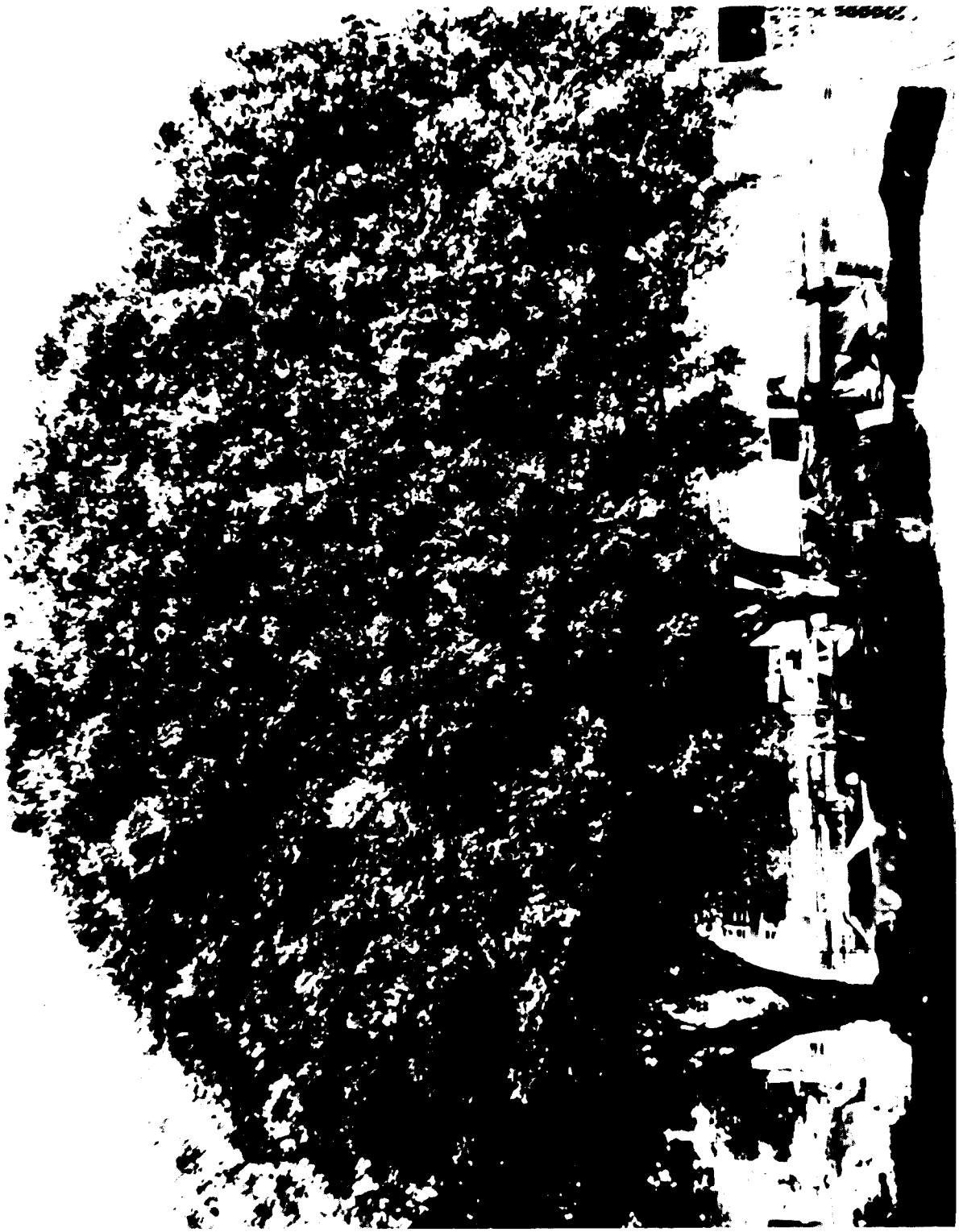

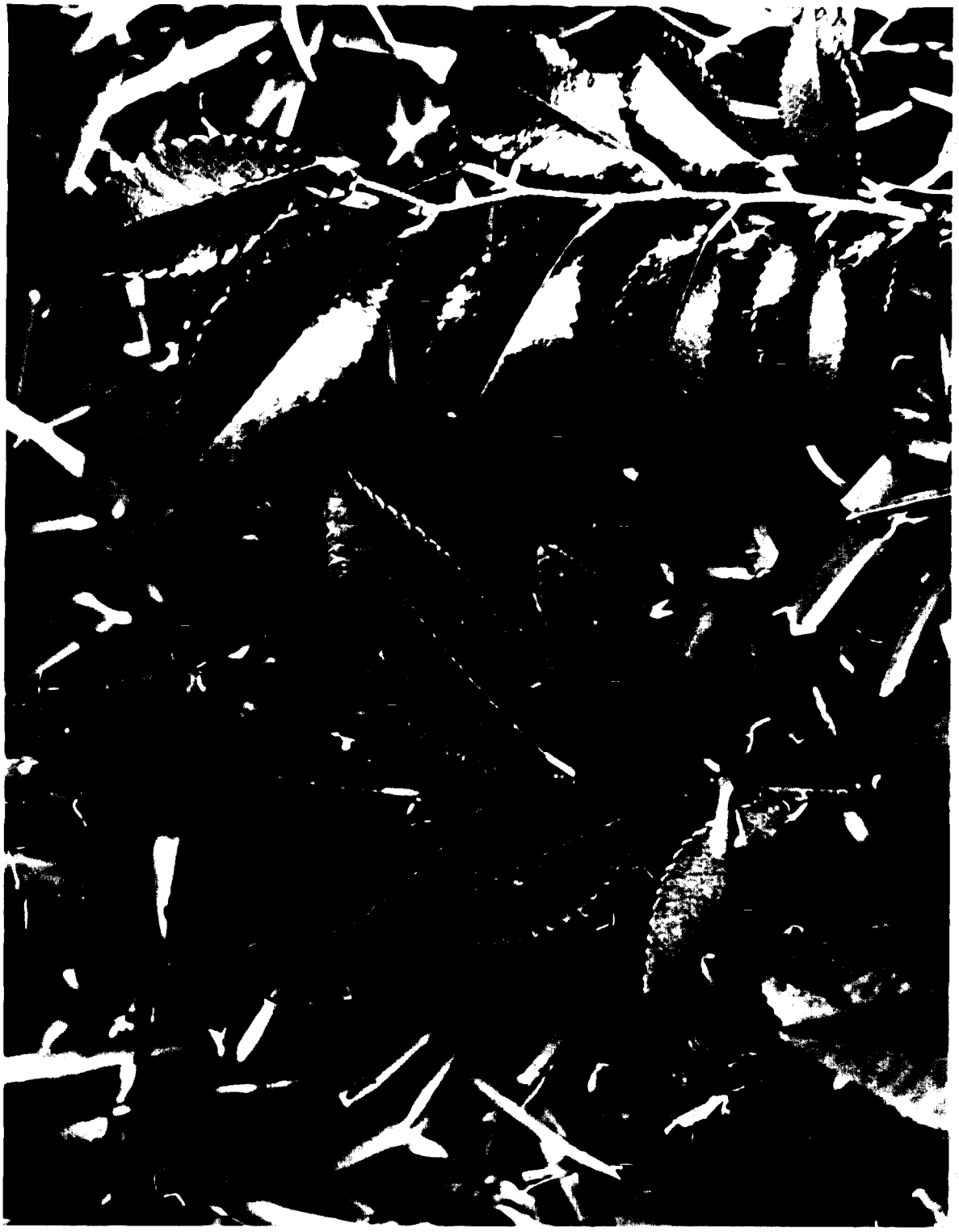

UNITED STATES PATENT AND TRADEMARK OFFICE

CERTIFICATE OF CORRECTION

PATENT NO. : PP 7,551

DATED : June 11, 1991

INVENTOR(S) : Glenn et al

It is certified that error appears in the above-identified patent and that said Letters Patent is hereby corrected as shown below:

On the title page:

[75] Inventors: Michael M. Glenn, Athens, GA.,
John H. Barbour, Atlanta, GA., and
Michael A. Dirr, Watkinsville, GA.

Signed and Sealed this

Twenty-seventh Day of April, 1993

*Attest:*

MICHAEL K. KIRK

*Attesting Officer*

*Acting Commissioner of Patents and Trademarks*